United States Patent
Hofman et al.

(10) Patent No.: US 8,815,179 B2
(45) Date of Patent: Aug. 26, 2014

(54) AUTOMATED ASEPTIC LIQUID COLLECTION WORKSTATIONS AND COLLECTION DEVICES THEREFORE

(75) Inventors: Jan Hofman, Vlaardingen (NL); Cleem Diemers, Soest (NL)

(73) Assignee: Alfa Wassermann, Inc., West Caldwell, NJ (US)

( * ) Notice: Subject to any disclaimer, the term of this patent is extended or adjusted under 35 U.S.C. 154(b) by 252 days.

(21) Appl. No.: 13/118,891

(22) Filed: May 31, 2011

(65) Prior Publication Data

US 2012/0138156 A1    Jun. 7, 2012

Related U.S. Application Data

(63) Continuation-in-part of application No. 12/959,647, filed on Dec. 3, 2010, now Pat. No. 8,640,556.

(51) Int. Cl.
*B01L 3/00* (2006.01)

(52) U.S. Cl.
USPC ............. 422/505; 422/50; 422/503; 422/504; 436/180

(58) Field of Classification Search
USPC ................. 222/642; 422/544, 50, 503–505; 436/180
See application file for complete search history.

(56) References Cited

U.S. PATENT DOCUMENTS

| | | | |
|---|---|---|---|
| 3,848,581 A | 11/1974 | Cinqualbre et al. | |
| 4,454,772 A | 6/1984 | Brunner et al. | |
| 4,691,850 A * | 9/1987 | Kirschmann et al. | 222/642 |
| 5,711,916 A | 1/1998 | Riggs et al. | 422/83 |
| 6,032,543 A | 3/2000 | Arthun et al. | 73/863.84 |
| 7,377,686 B2 | 5/2008 | Hubbard | |
| 7,381,375 B2 | 6/2008 | Ravkin et al. | |
| 7,467,890 B2 | 12/2008 | Patzek, IV | 366/165.1 |

(Continued)

FOREIGN PATENT DOCUMENTS

| | | |
|---|---|---|
| EP | 0086098 | 8/1983 |
| EP | 0637712 | 2/1995 |

(Continued)

OTHER PUBLICATIONS

Extended European Search Report dated Jul. 12, 2012 for European patent application No. 11009544.5.

(Continued)

*Primary Examiner* — Jyoti Nagpaul
(74) *Attorney, Agent, or Firm* — Ohlandt, Greeley, Ruggiero & Perle, LLP

(57) ABSTRACT

An automated liquid collection workstation is provided. The workstation includes a processor, a peristaltic pump, a valve actuator, and an algorithm. The peristaltic pump and the valve actuator are in electrical communication with the processor. The valve actuator can move a plurality of valves, when disposed therein, among an off position, a flush position, and a collection position. The algorithm is resident on the processor and is configured to: move all of the valves to the off position and place the pump in an off state when no sampling or flushing is required, move all of the valves to the flush position and place the pump in an on state for a predetermined flush time period when flushing is required, and move a respective one of the valves to the collection position, move any of the valves upstream of the respective valve to the flush position, and place the pump to the on state for a predetermined collection time period when collection is required.

18 Claims, 9 Drawing Sheets

(56) References Cited

U.S. PATENT DOCUMENTS

| | | | |
|---|---|---|---|
| 7,560,071 B2 | 7/2009 | Nichols et al. | 422/63 |
| 7,578,205 B2 | 8/2009 | Belongia | |
| 7,588,728 B2 | 9/2009 | Clark et al. | |
| 7,891,860 B2 | 2/2011 | Hubbard | |
| 7,921,740 B2 | 4/2011 | Furey et al. | |
| 8,007,743 B2 | 8/2011 | Clark et al. | |
| 2001/0010318 A1 | 8/2001 | Saveliev et al. | 222/148 |
| 2001/0048899 A1 | 12/2001 | Marouiss et al. | 422/100 |
| 2003/0116487 A1 | 6/2003 | Petersen | |
| 2007/0128087 A1 | 6/2007 | Cannizzaro et al. | 422/119 |
| 2008/0130405 A1 | 6/2008 | Hubbard | |
| 2010/0154569 A1 | 6/2010 | Guedon | |
| 2010/0269918 A1 | 10/2010 | Rudolph | |
| 2011/0024375 A1 | 2/2011 | Reinbigler et al. | |
| 2011/0201100 A1 | 8/2011 | Proulx et al. | |
| 2012/0000566 A1 | 1/2012 | Morrissey et al. | |
| 2012/0061332 A1 | 3/2012 | Kas et al. | |
| 2012/0223517 A1 | 9/2012 | Morrissey et al. | |
| 2012/0315189 A1 | 12/2012 | Scott et al. | |

FOREIGN PATENT DOCUMENTS

| | | |
|---|---|---|
| FR | 2358601 | 2/1978 |
| JP | 2003123268 A | 4/2003 |
| JP | 2005170288 A | 6/2005 |
| JP | 2007067968 A | 3/2007 |
| WO | 9009431 | 8/1990 |
| WO | 2007125023 | 11/2007 |
| WO | 2007125023 A1 | 11/2007 |

OTHER PUBLICATIONS

Japanese Office Action (English translartion) dated Jul. 30, 2013 for Japanese application No. 2011-265576.

Mexican Office Action (English translation) dated Mar. 20, 2014 for Mexican application No. MX/a/2011/012902.

* cited by examiner

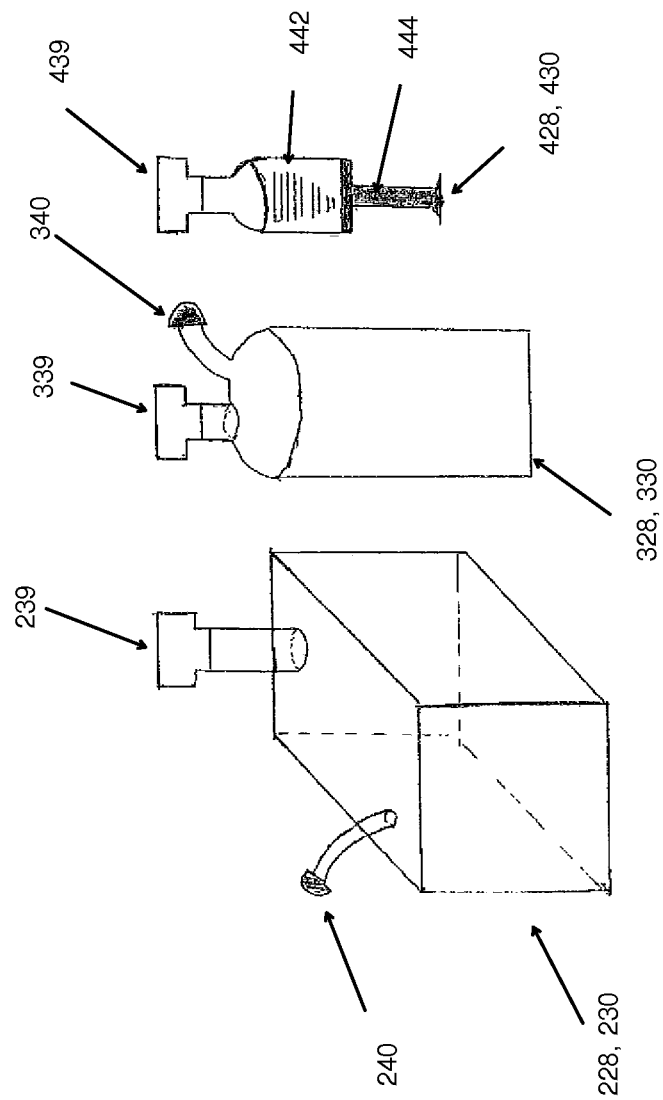

AUTOMATED ASEPTIC LIQUID COLLECTION WORKSTATIONS AND COLLECTION DEVICES THEREFORE

CROSS REFERENCE TO RELATED APPLICATIONS

This application is a continuation-in-part of application Ser. No. 12/959,647 filed Dec. 3, 2010, now pending, the entire contents of which are incorporated herein by reference.

BACKGROUND OF THE INVENTION

1. Field of the Invention

The present disclosure relates to automated aseptic liquid collection workstations. More particularly, the present disclosure relates to workstations for use in the automated collection of liquids during processing, as well as to collection devices used with such automated workstations.

2. Description of Related Art

The processing of many liquid products can be performed in a sterile environment and/or an aseptic environment to protect the product and/or the manufacturing personnel from contamination. Such liquid products can include, but are not limited to, pharmaceutical products (e.g., medicines and vaccines), food products, biological products, biochemical products, chemical products, and any combinations thereof.

It is known to collect liquid during the processing. The liquid collected can be used to sample or test the liquid product before, during, and after certain processing steps to ensure that the resultant product meets various acceptance criteria. Also, the collected liquid can be a finished product such as, but not limited to a collected centrifuged fraction or can be a finished product pre-cursor. Moreover, the collected liquid can be collect in any desired volume.

In some instances, the liquid collection can be performed during or after certain process steps and/or at certain time intervals. In other instances, the collection can be performed after the product has been made, but before the production batch is released for use by consumers.

Importantly, the collection of liquid from the processing line is a critical activity and creates a potential risk of contaminating the product and/or the sample. Unfortunately, the risk of contamination often leads manufacturers to limit the number of times liquids are collected and/or to limit the number of locations where such liquids are collected.

In addition, when collecting product testing samples, contamination of the sample may cause a false result, which can lead to the unneeded destruction of a product batch and/or unneeded delay in the continuation of the production process until the cause of the contamination is determined. Further, the need to clean and sterilize the sample path before and/or after each batch typically requires the sampling devices to be hard piped into a specific location in the production line, which can limit the flexibility of the processing line to process other products in a timely and efficient manner.

Further, the containers of collected liquids must be properly identified by the operator and this identifying information must then subsequently be input by the department responsible for testing the sample or releasing the finished product. The manual identification of collected liquid containers and the manual input of this identity have proven to be error prone, which can further complicate the proper testing and release of product.

Accordingly, it has been determined by the present disclosure that there is a need for workstations that can overcome, alleviate, and/or mitigate one or more of the aforementioned and/or other deleterious effects of the prior art. For example, it has been determined by the present disclosure that there is a need for workstations that automate the collection of liquid products, while ensuring integrity and eliminating the risk of contamination, and minimizing errors related to manual input of data related to the collected liquid.

BRIEF SUMMARY OF THE INVENTION

A liquid collection device is provided. The collection device includes an input conduit, a plurality of automated product collection containers, a waste collection container, and a valve block. The input conduit is connectable to a liquid processing line. The product collection containers each have a product volume and the waste collection container has a waste volume. The valve block a plurality of three-way valves and an output, where the plurality of three-way valves correspond in number to the plurality of product collection containers, each of the three-way valves placing the input conduit in liquid communication with a different one of the plurality of product collection containers. The output is in liquid communication with the waste collection container. The collection device has a ratio of the waste volume to the product volume of not more than 15:1.

An automated liquid collection workstation is provided. The workstation includes a processor, a peristaltic pump, a valve actuator, and an algorithm. The peristaltic pump and the valve actuator are in electrical communication with the processor. The valve actuator can move a plurality of valves, when disposed therein, among an off position, a flush position, and a collection position. The algorithm is resident on the processor and is configured to: move all of the valves to the off position and place the pump in an off state when no collection or flushing is required, move all of the valves to the flush position and place the pump in an on state for a predetermined flush time period when flushing is required, and move a respective one of the valves to the collection position, move any of the valves upstream of the respective valve to the flush position, and place the pump to the on state for a predetermined collection time period when collection is required.

A method of automatically taking a plurality of liquid collections from a processing line is provided. The method includes: cleaning a processing line having a first half of a two-part connector connected thereto; connecting a second half of the two-part connector to the first part, the second half part of a liquid collection device, the liquid collection device having a plurality of collection containers, a valve block, and an input conduit with the second half of the two-part connector, the valve block having an input, a plurality of three-way valves, and an output, the plurality of three-way valves corresponding in number to the plurality of collection containers, each of the three-way valves placing the input in liquid communication with a different one of the plurality of collection containers, the output being in liquid communication with a waste collection container, the input being in liquid communication with the input conduit; and inserting the valve block into a valve actuator so that a handle of each of the plurality of valves is movable by the valve actuator.

A method of automatically taking a plurality of liquid collections from a processing line is also provided that includes: placing an input conduit of a liquid collection device in liquid communication with the processing line; operatively coupling the input conduit to a peristaltic pump and to an input of a valve block having a plurality of three-way valves; operatively coupling the valve block to a valve actuator so that each of the plurality of three-way valves is movable by a different portion of the valve actuator among an off position, a flush position, and a collection position; controlling the valve actuator to move all of the plurality of three-way valves to the flush position and turning on the peristaltic pump so that liquid from the processing line is pumped through the valve block to a waste container in liquid communication with an output of the valve block; and controlling the valve actuator to move a particular valve of the plurality of three-way valves to the collection position and to move any of the plurality of three-way valves upstream of the particular valve to the flush position while the peristaltic pump remains on, the particular valve being associated with a particular collection container so that liquid from the processing line is pumped through the valve block to the particular collection container.

The above-described and other features and advantages of the present disclosure will be appreciated and understood by those skilled in the art from the following detailed description and drawing.

BRIEF DESCRIPTION OF THE SEVERAL VIEWS OF THE DRAWINGS

FIGS. 9a through 9c illustrate alternate exemplary embodiments of liquid collection containers and/or waste collection containers for use with the liquid collection set of FIG. 5.

DETAILED DESCRIPTION OF THE INVENTION

Figure 1:
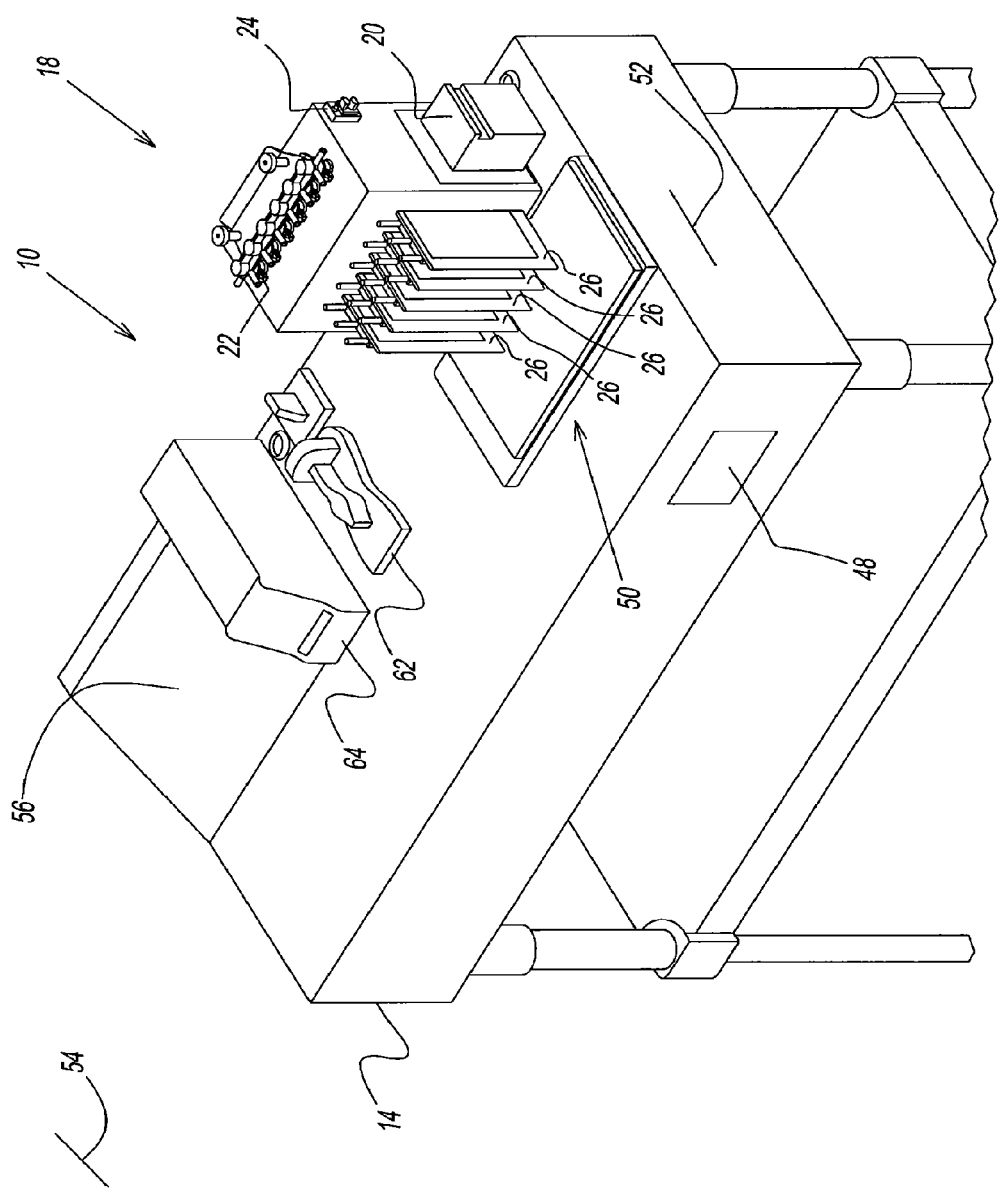
FIG. 1 is a front, top perspective view of an exemplary embodiment of a workstation according to the present disclosure.
Figure 2:
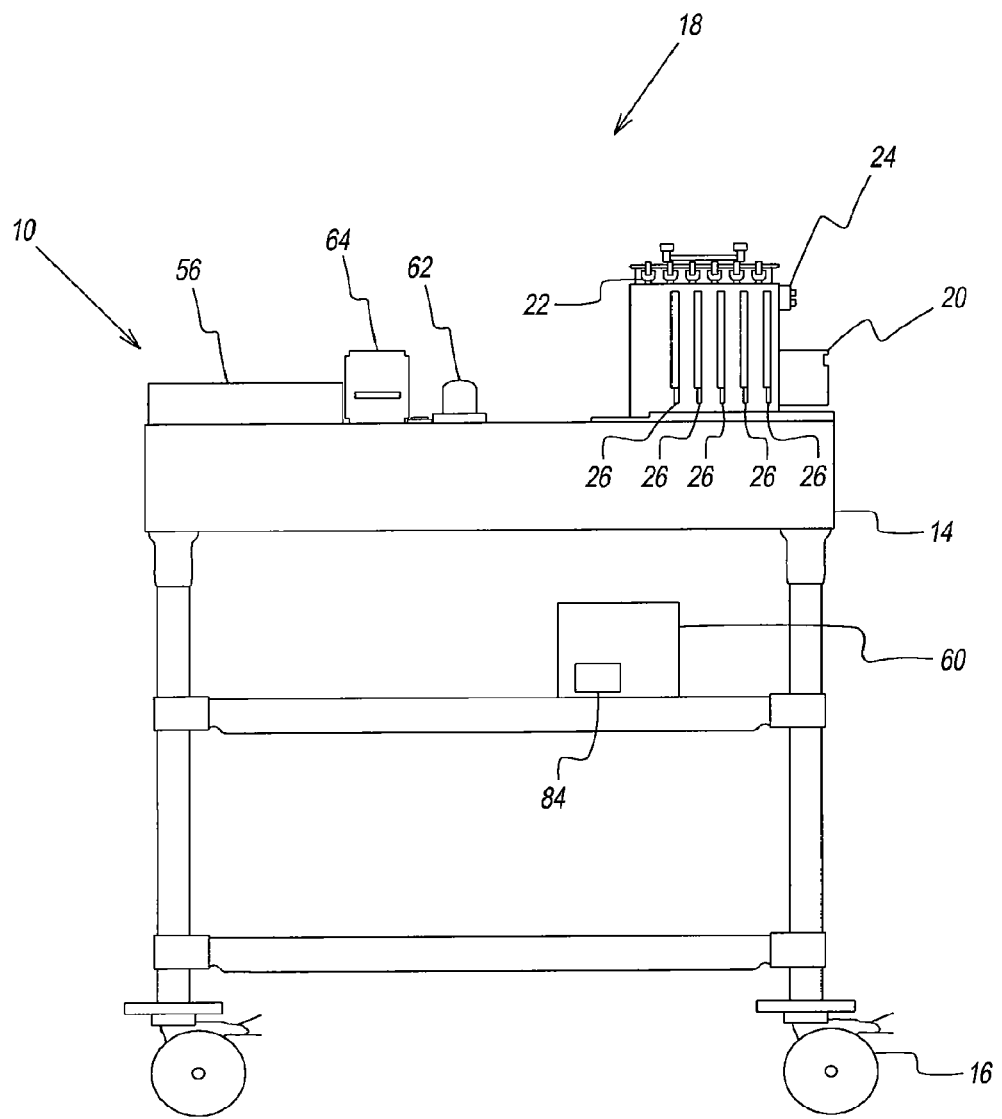
FIG. 2 is a front plan view of the workstation of FIG. 1.
Figure 3:
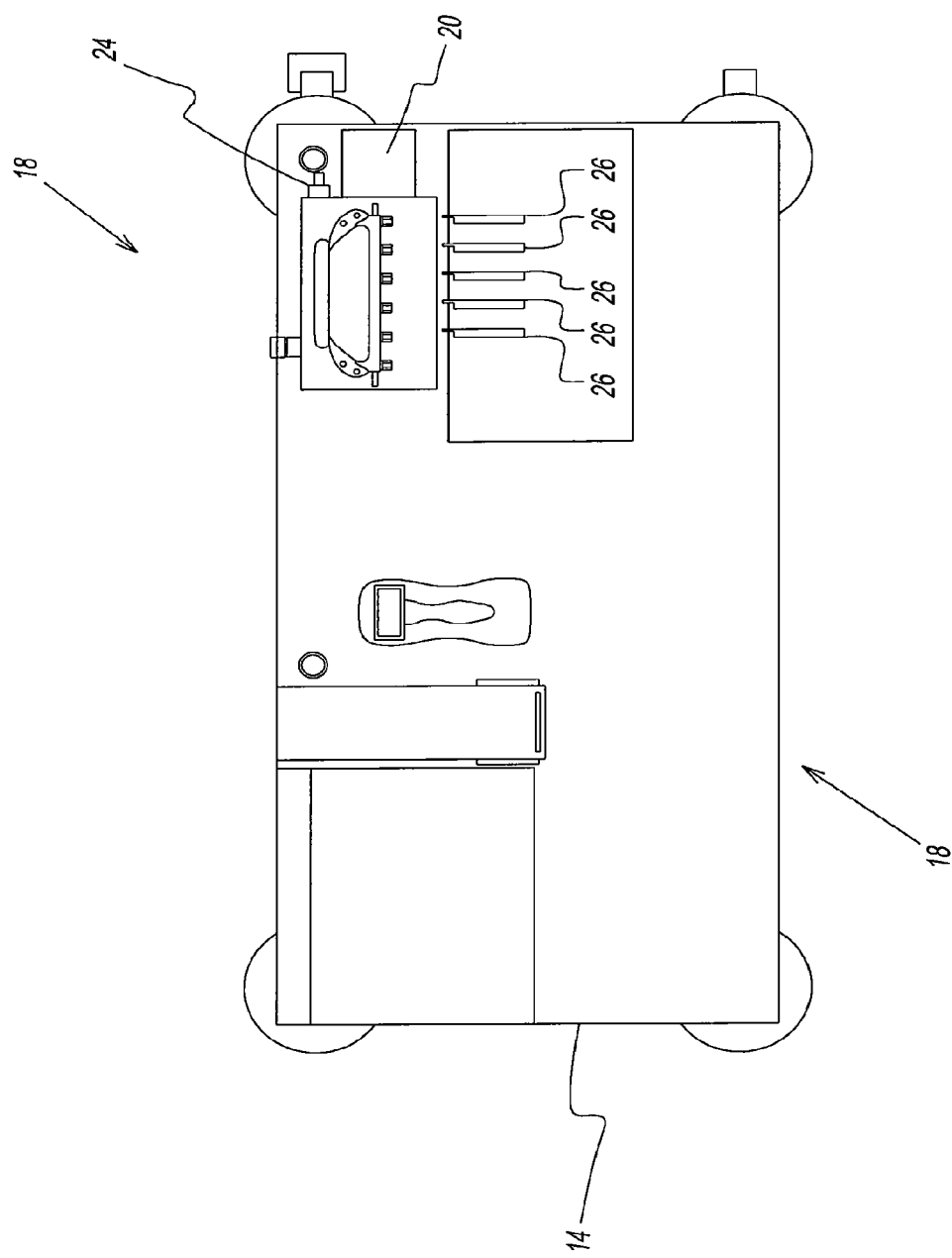
FIG. 3 is a top view of the workstation of FIG. 1.
Figure 4:
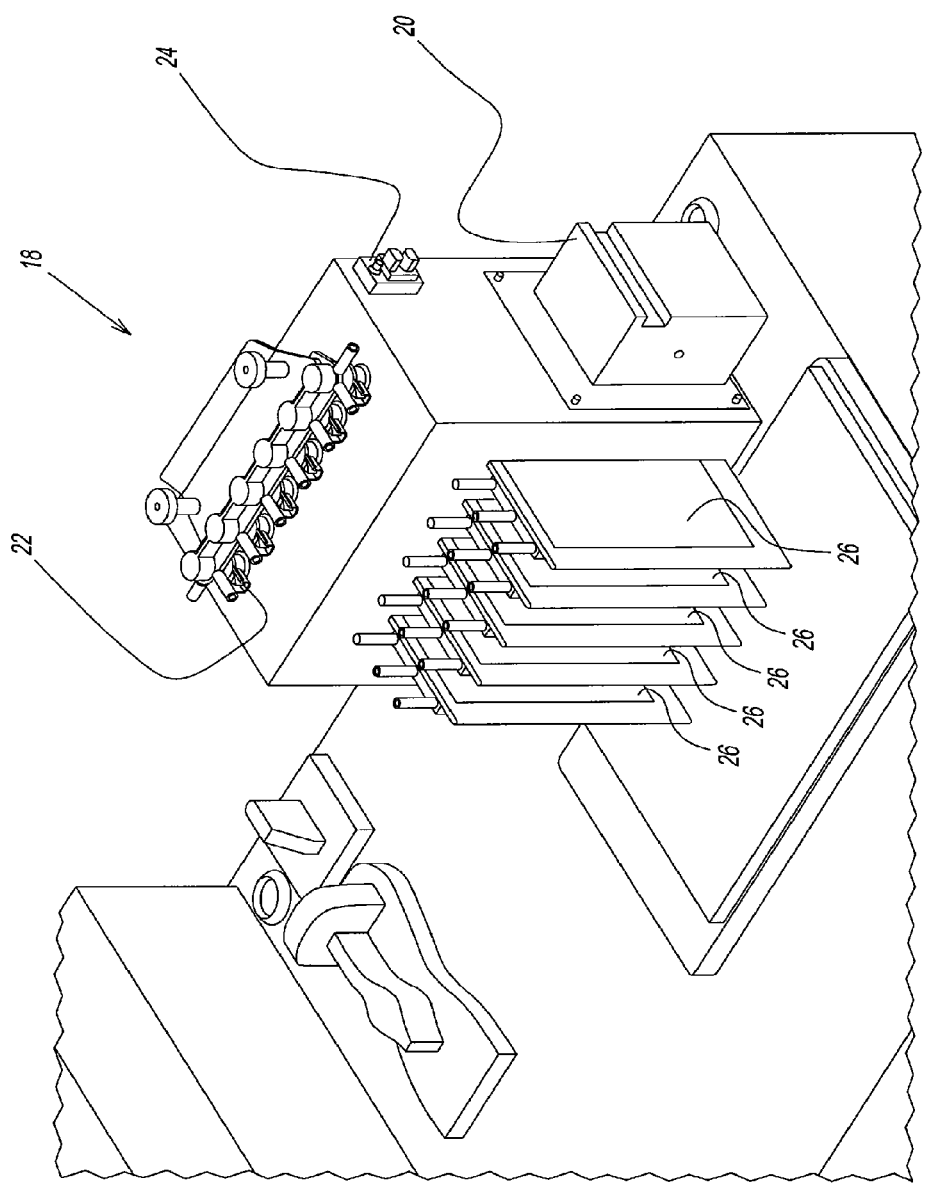
FIG. 4 is a front, top perspective view of an exemplary embodiment of a collection portion of the workstation of FIG. 1.

Referring to the figures, and in particular to FIGS. 1 through 4, an exemplary embodiment of an automated aseptic liquid collection workstation according to the present disclosure is shown and is generally referred to using reference numeral 10. Workstation 10 is configured to automatically aseptically collect, label, and store, in liquid collection device 12 (shown in FIG. 5), a plurality of liquid collections from a processing line or vessel (A).

Workstation 10 is configured to automatically collect liquids such as, but not limited to, pharmaceutical products (e.g., medicines and vaccines), food products, biological products, biochemical products, chemical products and any combinations thereof. The collected liquid can be used as a sample, as an intermediate product, or as a finished product.

Advantageously, workstation 10 is flexibly configured, namely is configured so that the workstation can be moved from point-to-point and/or from one process step to another process step in a manufacturing process. Further, workstation 10 is preferably suitable for use in an aseptic or clean room environment such that the material selection (e.g., stainless steel or other material) and material specifications (e.g., surface finish) are sufficient for use in such environments.

Workstation 10 includes a base or cabinet 14 supported, in some embodiments, by a plurality of wheels or casters 16 such that the workstation is mobile and can be positioned, as desired, in various locations within a processing facility.

Workstation 10 is includes collection portion 18 for pumping liquid into collection device 12. Collection portion 18 includes a pump 20, a valve actuator 22, in some embodiments, a liquid edge detector 24, and a plurality of liquid holding areas 26.

Pump 20 can be any desired pumping device but is, preferably, a non-contact pump that selectively draws liquid without directly contacting the liquid itself. In a preferred embodiment, pump 20 is a peristaltic pump.

Liquid edge detector 24 can be any desired detector such as, but not limited to a sonic, a capacitance, or any other non-contacting or contacting sensor for determining the presence and absence of liquid in one or more areas of liquid collection device 12. Detector 24 can be in electrical communication with workstation 10 so that the workstation can detect when liquid is present in a predetermined location in liquid collection device 12.

Figure 5:
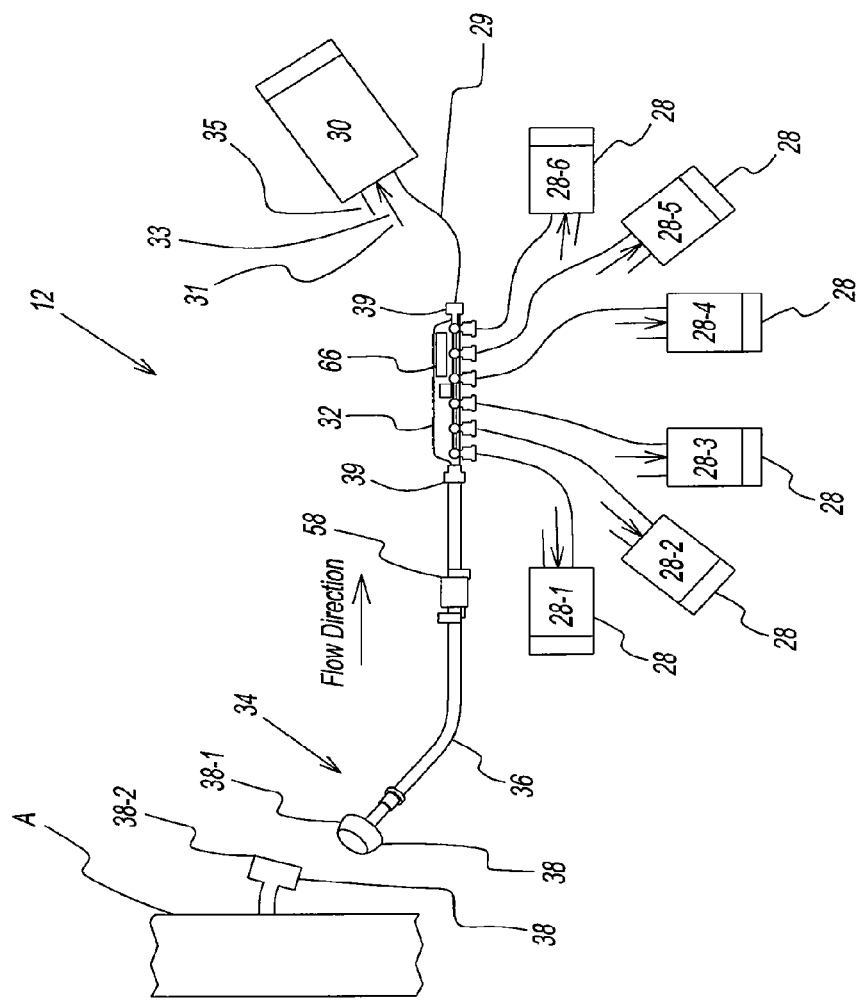
FIG. 5 is a perspective view of an exemplary embodiment of a liquid collection set according to the present disclosure for use with the workstation of FIG. 1.

As seen in FIG. 5, liquid collection device 12 includes a plurality of product collection containers 28 (six shown), at least one waste container 30 (only one shown), and a valve block 32. Product containers 28 can be configured to have any desired volume so that the volumes of the product containers are identical to one another and/or different from one another.

Product collection containers 28 and waste containers 30 can be any desired collection container such as, but not limited, collection bags as shown in FIG. 5. For example, containers 28, 30 can be collection bags such as the Allegro™ 2D Biocontainer, which is commercially available from Pall Corporation. In this embodiment, each container 28, 30 includes an input line 29 releasably sealed with a clamp 33, an output line 31 releasably sealed with a clamp 33, and a port 35.

Of course, it is contemplated by the present disclosure for containers 28, 30 to be any sterile collection container including, but not limited to, collection bottles, collection boxes, collection syringes, and others.

In the illustrated embodiment, liquid collection device 12 includes five automated product collection containers 28 of identical volume, e.g., about 50 milliliters (mL), and one manual collection container 28 of a larger volume, about 500 ml. Also, in the illustrated embodiment, the liquid collection device 12 includes one waste container 30 of about 1,000 mL. Of course, it should be recognized that the number and volumes of containers 28, 30 can be modified to any desired size.

Device 12 further includes an input conduit 34 configured to place the processing line in liquid communication with valve block 32.

Input conduit 34 includes at least one flexible portion 36. Portion 36 is configured to operably mate with pump 20 so that the pump can force the liquid into containers 28, 30 of liquid collection device 12. In the example where pump 20 is a peristaltic pump, flexible portion 36 is made of a material having sufficient resiliency (e.g., silicone tubing) to operate in cooperation with the peristaltic pump.

Liquid collection device 12 finds use with one or more two-part, aseptic connectors 38. In the illustrated embodiment, input conduit 34 has only one part 38-1 of a two-part connector 38 connected thereto. The mating part 38-2 for two-part connector 38 of input conduit 36 is in liquid communication with processing line or vessel A.

In this manner, liquid collection device 12 can be liquidly connected to the processing line or vessel by joining both halves 38-1, 38-2 of two part-connector 38 at the input conduit and the processing line or vessel to one another. In order to maintain sterility, the portion of the two-part connector 38-2 mated with the production line or vessel A can be sterilized or sanitized along with the production line or vessel before processing of the liquid.

Two-part connector 38 can be any disposable, two-part aseptic connector such as, but not limited to the Kleenpak™ connector, which is commercially available from Pall Corporation, the Opta® SFT-I connector, which is commercially available from Sartorius Stedim Biotech, the Lynx® ST connector, which is commercially available from Millipore Corporation, and the AseptiQuik™ connector, which is commercially available from Colder Products Corporation.

In some embodiments of liquid collection device 12, product collection containers 28, waste collection container 30, and valve block 32 are removably connected to one another. For example, liquid collection device 12 can include a plurality of connectors 39 such as, but not limited to Luer lock connectors.

All product contact surfaces within collection device 12 are made of any material sufficient to hold or contact the liquid without interacting or contaminating the liquid. Moreover, collection device 12 can be packaged within one or more outer wrappings (not show) then can be sterilized using known sterilization methods such as, but not limited to, gamma irradiation. In this manner, collection device 12 can remain in a sterile condition until ready for use.

Figure 6:
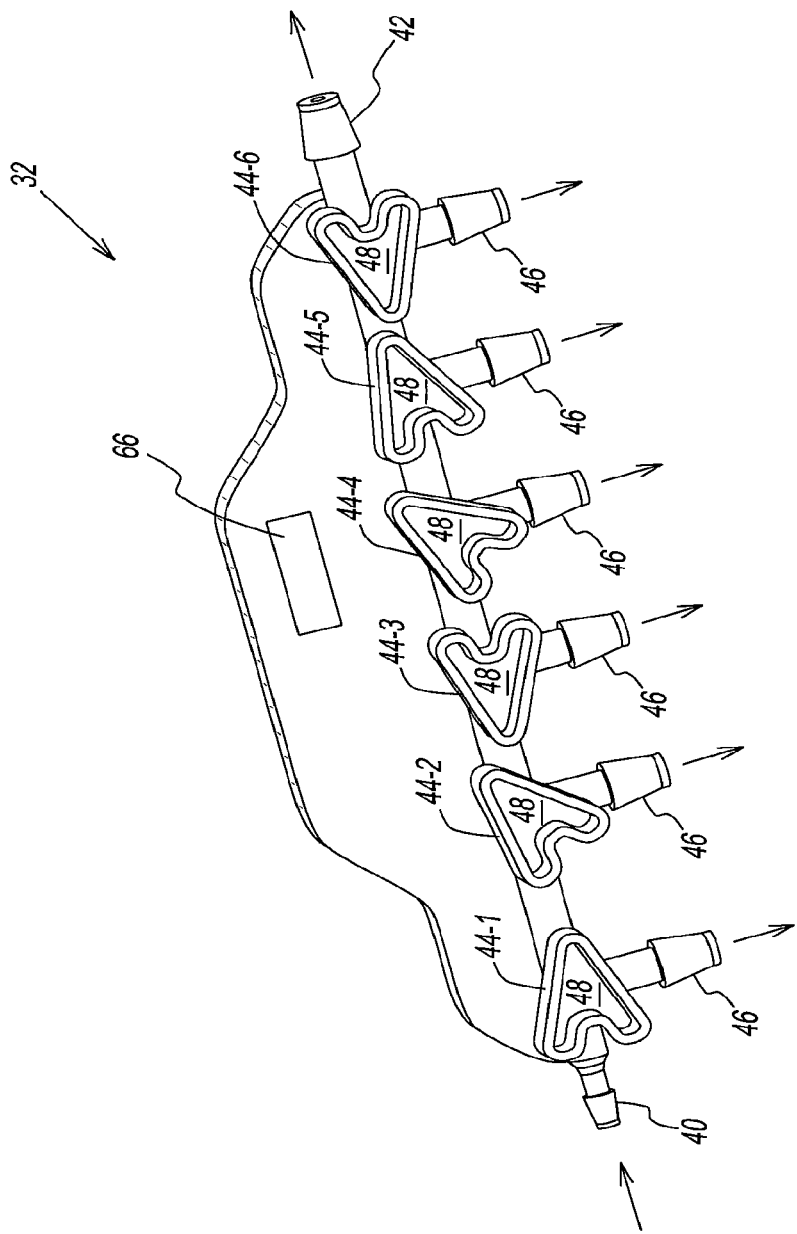
FIG. 6 is a perspective view of an exemplary embodiment of a valve block according to the present disclosure for use in the liquid collection set of FIG. 5.

Valve block 32, as shown in FIG. 6, includes an input 40, a waste output 44, and a plurality of three-way valves 46 (six shown). The input 40 is in liquid communication with input conduit 34 and waste output 42 is in liquid communication with waste collection container 30.

The plurality of three-way valves 44 correspond in number to the plurality of collection containers 28, with an output 46 from each of the valves being in liquid communication with a different collection container 28.

Three-way valves 44 are each movable by rotation of a valve handle 48 among three positions: an "off" position; a "flush" position; and a "collection" position.

In the off position, each valve 44 prevents liquid from input 40 from flowing through the valve to either waste output 42 or output 46. In the flush position, each valve 44 allows liquid from input 40 to flow through the valve towards waste output 42, but prevents flow toward its respective output 46. In the collection position, each valve 44 allows liquid from input 40 to flow through the valve towards the respective output 46, but prevents flow toward the waste output 42.

Handle 48 of each valve 44 operably mates with a different portion of valve actuator 22 so that the valve actuator can selectively rotate each handle independently of one another among the three positions. In this manner, workstation 10, via valve actuator 22, is configured to actuate valve block 32 to selectively divert liquid from the processing line or vessel into any one of collection containers 28 or waste container 30.

Referring now to Table No. 1 below, the relative positions of valves 44 are provided during various sampling activities contemplated by the present disclosure.

Here, the plurality of valves 44 are sequentially numbered, in the direction of liquid flow, as valves 44-1 through 44-6 and the collection containers 28 are sequentially numbered, in the direction of liquid flow, as containers 28-1 through 28-6.

TABLE NO. 1

| | VALVE POSITION | | | | | |
|---|---|---|---|---|---|---|
| | Valve 44-1 | Valve 44-2 | Valve 44-3 | Valve 44-4 | Valve 44-5 | Valve 44-6 |
| Not in use | Off | Off | Off | Off | Off | Off |
| Flush to waste container 30 | Flush | Flush | Flush | Flush | Flush | Flush |
| Divert to container 28-1 | Divert | Off | Off | Off | Off | Off |
| Divert to container 28-2 | Flush | Divert | Off | Off | Off | Off |
| Divert to container 28-3 | Flush | Flush | Divert | Off | Off | Off |
| Divert to container 28-4 | Flush | Flush | Flush | Divert | Off | Off |
| Divert to container 28-5 | Flush | Flush | Flush | Flush | Divert | Off |
| Divert to container 28-6 | Flush | Flush | Flush | Flush | Flush | Divert |

As seen in Table No. 1 above, when liquid collection device 12 is not in use, all of the valves 44 are rotated to the "off" position, preventing liquid communication through valve block 32.

Before collection and/or whenever it is desired to flush or prime the liquid flow path within liquid collection device 12, each of the valves 44 can be rotated to the "flush" position, placing input 40 in liquid communication with output 42. In this manner, liquid from input conduit 34 is diverted to waste container 30.

When diversion of liquid to a particular collection container 28 is desired, the particular valve 44 associated with that particular container 28 is moved to the "collection" position. Further, any valve upstream, with respect to liquid flow through valve block 32, is moved to the flush position. Preferably, any valve 44 downstream, with respect to liquid flow through valve block 32, is moved to the off position. However, these downstream valves 44 can have any desired state.

When the diversion to a particular collection container 28 is completed, valves 44 are returned to the "off" position.

In use, liquid collection device 12 is positioned in workstation 10 so that flexible portion 36 of input conduit 34 is operatively positioned in pump 20 and so that valve block 32 is operatively positioned in valve actuator 22. When liquid is being process through the production line or vessel, the half of two-part connector 38 at input conduit 34 is operatively connected to its mating half arranged on the line or vessel.

Valve actuator 22 can be used by the operator to manually operate valves 44. For manual operation, workstation 10 includes one or more valve operating buttons or controls 48.

Alternately, and in a preferred embodiment, valve actuator 22 can be automatically controlled by workstation 12 as described in more detail herein below. Of course, it is contemplated by the present disclosure for valve actuator 22 to be controlled by any combination of manual and automated control.

It has been determined by the present disclosure that workstation 10, due to in part the use of two-part, aseptic connectors 38 in combination with liquid collection device 12, can be selectively moved from point-to-point within the manufacturing process to perform the desired sampling as needed. Also, workstation 10 can be installed in a particular location within the manufacturing line when that line is set up to make a first product, but can then be relocated to a different location within the manufacturing line when that line is set up to make a second product. In other words, workstation 10 can reduce the equipment cost to monitor a manufacturing process by being used in multiple locations within the manufacturing line during a production run or by being repositioned to a different stationary position when the manufacturing line is reconfigured to accommodate the manufacture of different products.

Workstation 10 can, in some embodiments, include a product and waste container holding area 50, which can maintain containers 28, 30 in a desired position and/or in a desired conditions suitable for the liquid contained therein. For example, workstation 10 can include environmental controls sufficient to maintain containers 28, 30, and thus, liquid contained therein, at a desired temperature. In other examples, workstation 10 can include agitation and/or vibration devices sufficient to maintain the liquid within containers 28, 30 in a mixed or agitated state.

Workstation 10 can include one or more sensors 52 to monitor and record the conditions (e.g., temperature, humidity) within base 14, the conditions within containers 28, 30 (e.g., temperature, turbidity, volume, etc), and other conditions of the workstation. Additionally, workstation 10 can include sensors or can connect to sensors outside 54 the workstation to monitor and records the conditions outside the base 12 including but not limited to temperature, pressure, humidity, particulates, and detection, typing and monitoring of viral and/or microbial organisms.

It is contemplated by the present disclosure for workstation 10 to coordinate the control of pump 20, valve actuator 22, liquid edge detector 24 and sensors 50 within workstation 10 as well as collection of signals and data from any other (wireless or hardwire connected) human-machine input devices 56 such as, but not limited to, keyboards, and touch screens or any other data communication devices, USB or other data communication ports, CD or other data reading devices, computers, PLC's, analyzing equipments, testing devices and sensors outside the workstation.

In some embodiments, liquid collection device 12 can include a disposable flow meter 58 in electrical communication with workstation 10.

Thus, workstation 10 can include a processor 60 having human-machine-interface (HMI) 56 with one or more input devices 62 and one or more output devices 64. Processor 60 can include devices such as, but not limited to, a computer, a programmable logic controller (PLC), or any other processor suitable to control the various components of workstation 10.

HMI 56 can includes, for example, a keyboard, a mouse, a bar-code reader, a touch screen, a USB or other data communication port, CD or other data reading device, a remote control, or any other data communication device suitable for inputting commands to processor 60 in a wired and/or a wireless manner, and any combinations thereof.

Output device 64 can include a computer monitor, an audible alarm device, a visual alarm device, a printer, a USB or other data communication port, a CD or other data writing device, a (wireless or hard-wired) data communication device or any other device suitable for receipt of a wired and/or a wireless output from processor 60.

In a preferred embodiment, HMI 56 includes at least one bar code reader 62 and liquid collection device 12 can include at least one machine readable label 66, which includes details regarding the liquid collection device such as, but not limited to, the lot number, the expiration date, the number of product and waste containers 28, 30, the volume of product and waste containers 28, 30, the volume of conduits within the collection device, and other details. In use, the operator can scan machine readable label 66 of liquid collection device 12 using bar code reader 62 so that processor 60 can determine and record the various details regarding the liquid collection device 12.

Further, it is contemplated by the present disclosure for output devices 64 to include at least one printer. Processor 60 controls printer 64 to print labels, which can be applied by the operator directly on each container 28, 30 and includes information that is relevant to the liquid contained within the container. For example, processor 60 can control printer 64 to print information such as, but not limited to, date of collection, time of collection, operator, batch ID, program sequence, room number, station number, collection location, and other process or environmental variables.

Preferably, printer 64 is configured to print information on the label in a machine readable language, such as a bar code, so that a laboratory technician can scan the machine readable code to input all relevant data related to the liquid within the container, which can mitigate instances of data entry errors.

Processor 60 is in electrical communication via any wireless or wired manner such as, but not limited to, electrical, optical, audible, infrared, radiofrequency, magnetic and other means of communication with any one or more of pump 20, valve actuator 22, level sensor 24, manual controls 48, sensors 52 and 54, HMI 56, flow meter 58, output devices 60, as well as bar code reader 62 and printer 64.

In this manner, processor 60 is configured to coordinate the control of workstation 10 and the collection of liquid in collection device 12, as well as to provide information on labels for placement onto containers 28, 30.

In some examples, processor 60 can communicate in wired and/or wireless manner with one or more computers (not shown) external to workstation 10, where such external computers can include data collection, data archiving, data analysis and data management software.

The aseptic liquid collection ability of workstation 10 and collection device 12 mitigate or eliminate the risk of contaminating the collected liquid or the processing line.

Workstation 10, via processor 60, can be programmed to aseptically obtain one or a series of liquid collections taken randomly, at manual selected times or at pre-set times and with manually selected volumes or pre-set volumes.

Figure 7:
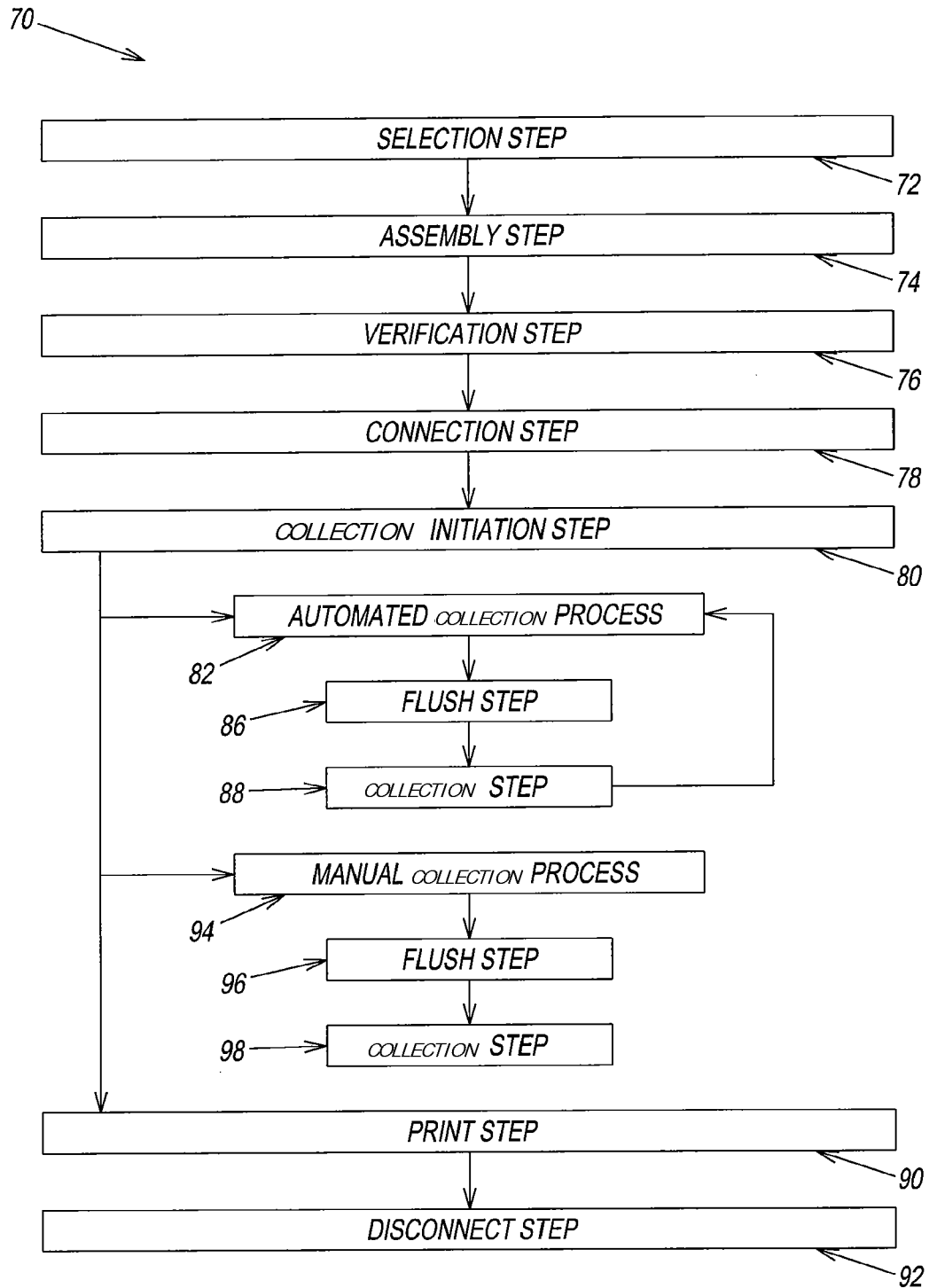
FIG. 7 is a flowchart illustrating an exemplary embodiment of a liquid collection method according to the present disclosure.

Referring now to FIG. 7, a method 70 of operating workstation 10 having liquid collection device 12 is shown.

In a first or selection step 72, the appropriate liquid collection device 12 for desired collection is selected by the operator.

In a second or assembly step 74, the operator assembles the selected liquid collection device 12 in workstation 10. Specifically, containers 28, 30 are placed in area 50, valve block 32 is operatively positioned in valve actuator 22, and flexible portion 36 of input conduit 34 is operatively positioned in pump 20. When level liquid edge detector 24 is present, a portion of input conduit 34 is operatively positioned in the detector.

In a third or verification step 76, the operator inputs information related to the liquid collection device 12 into processor 60 and inputs information related to the desired processing line or vessel from which workstation 10 will be collection the liquid. In some embodiments, the verification step 76 includes requiring the operator to use scanner 62 to scan bar code 66 on liquid collection device 12.

Once processor 60 verifies liquid collection device 12, the processor sends an output to the operator in a fourth or connection step 78 to instruct the operator to place the liquid collection device in liquid communication with the processing line or vessel via HMI 56. As discussed in detail above, liquid collection device 12 is placed in liquid communication with the processing line or vessel by interconnecting two-part connector 38.

When the liquid is present in the processing line or vessel, the operator initiates a desired collection sequence of workstation 10 during step 80. Step 80 may initiate a manual collection process 82 using manual controls 48. Alternately, step 80 may initiate an automated collection process using an algorithm 84 resident on processor 60.

During automated collection, algorithm 84 is configured to activate pump 20 to force liquid from the processing line or vessel through input conduit 34 and valve block 32 and into, as desired, any one of containers 28 and waste container 30.

Before taking each collection, algorithm 84 is configured to control workstation 10 to a flush step 86. During flush step 86, algorithm 84 flushes or purges liquid through liquid collection device 12 into waste container 30 for a predetermined period of time by moving all of the valves 44 to the "flush" position.

Then, after the predetermined purge or flush of step 86, algorithm 84 initiates a collection step 88 in which the processor 60 moves the plurality of valves 44 in the manner discussed above with respect to Table No. 1 to divert a desired volume of liquid into the desired collection container 28.

After a predetermined volume of liquid has been diverted into the selected collection container 28, algorithm 84 completes the collection step 88 by deactivating pump 20 and returning the valves 44 to the "off" position.

Algorithm 84 repeats the flush and collection steps 86, 88 to activating pump 20 to flush liquid within liquid collection device 12 to waste container 30, divert the liquid to the desired product container 28, deactivates the pump, and closes the valves until all of the desired liquid collections have been obtained.

In embodiments where liquid collection device 12 includes flow meter 58, algorithm 84 can use inputs from the flow meter to ensure proper liquid and purge volumes. Similarly, in embodiments where workstation 10 includes liquid edge sensor 24, algorithm 84 can use inputs from the sensor to ensure proper liquid and purge volumes.

Preferably, algorithm 84 is further configured to activate printer 64 to print data onto a label when a respective collection of liquid is obtained during a print step 90. The operator can then apply the label on the appropriate container 28, respectively. Similarly, algorithm 84 can be configured to activate printer 64 to print waste related data onto a label when the respective waste is collected or after all of the waste has been collected.

During manual collection process 94, the operator can manually and/or via controller 60 flush liquid collection device 12 to waste container 30 during a manual flush step 96 and divert a desired volume of liquid to the manual container 28, when present, during a manual collection step 98.

Once all of the collections of liquid have been obtained, the operator can, during a disconnection step 92, disconnect liquid collection device 12 from the processing line or vessel by separating two-part connector 38. Similarly, the operator can remove each product container 28 and waste container 30 from liquid collection device 12 by separating two-part connectors 38.

Advantageously, algorithm 84 purges a predetermined amount liquid from with liquid collection device 12 before taking each collection of liquid to ensure that the liquid collected in product container 28 is representative of liquid in the processing line or vessel at the time of the collection.

In order to perform the desired purging, waste container 30 has a volume that is sufficient to hold the purged liquid. In the illustrated embodiment, a ratio of the volume of the waste container 30 to the volume of the product container 28 is not more than 15:1, more preferably 10:1, with between 5:1 to 2:1 being most preferred. In this manner, waste container 30 provides a volume sufficient to allow liquid collection device 12 to be flushed before taking each of the collections to ensure that the liquid collected in the product container 28 is representative of the liquid in the processing line and, not, liquid remaining within the liquid collection device from the prior diverted liquid.

Figure 8:
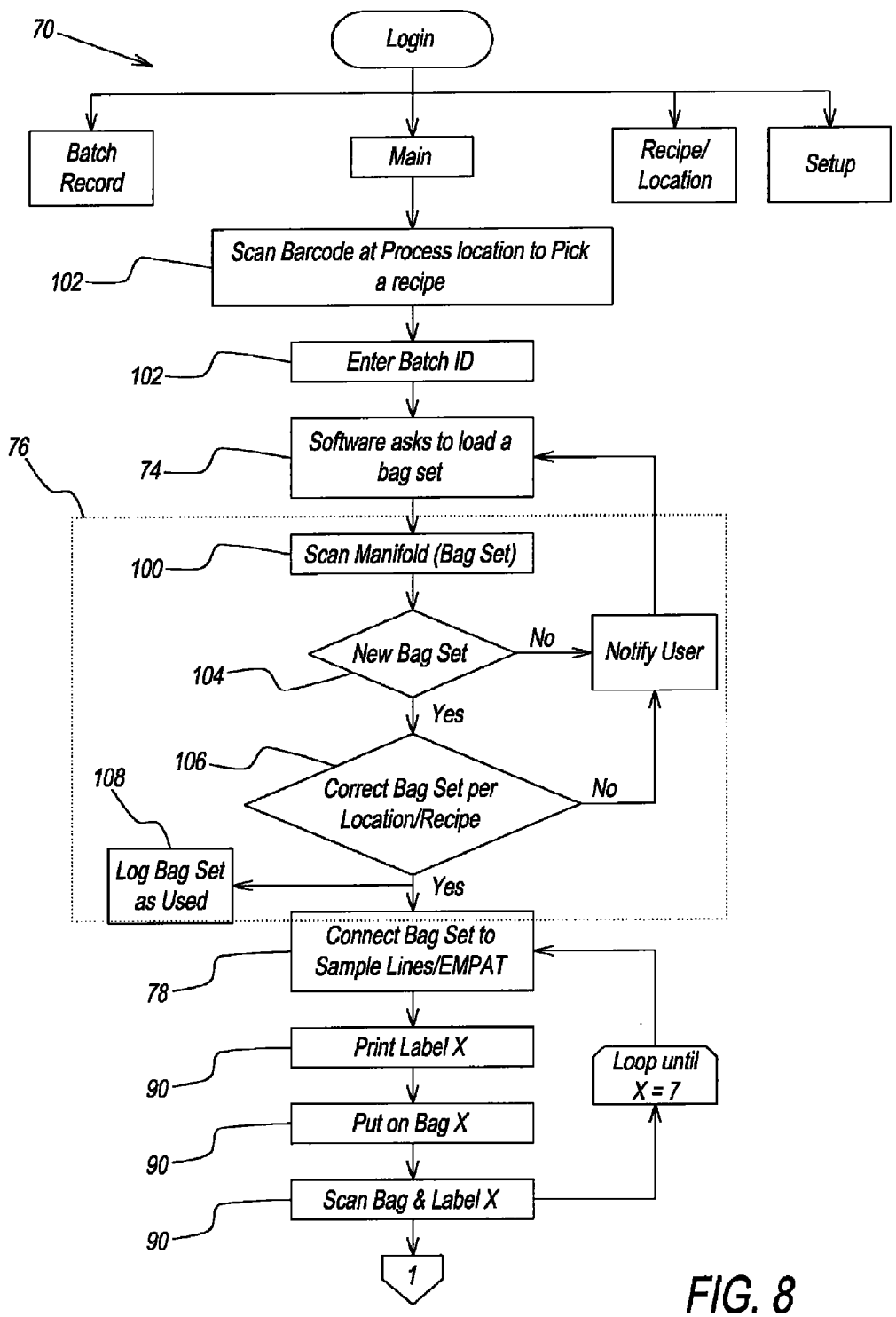
FIG. 8 is a flowchart illustrating an exemplary embodiment of a collection device verification method according to the present disclosure.

Referring now to FIG. 8, an exemplary embodiment of verification step 76 from method 70 is shown in more detail. During verification step 76, processor 60 requires the user to scan bar code 66 on liquid collection device 12 using scanner 62 in a scanning step 100.

In some embodiments, prior to scanning step 94, method 70 can further include a process identification step 102, where parameters and/or details of the process and/or liquid to be collected are entered into processor 60. The parameters and/or details can be entered manually into processor 60 by the operator, can be scanned into processor 60 using scanner 62 and an identifier located on the batch record and/or the process equipment, or any combination of manual and scanning data entry.

Verification step 76 determines, based on data within processor 60 and information from bar code 66, whether liquid collection device 12 is new or has been previously used at a step 104. If the liquid collection device 12 has been previously used, verification step 76 returns the user to assembly step 74 so that a new collection device can be used.

If the liquid collection device 12 is new, verification step 76 compares the details of the liquid collection device (e.g., size and number of containers 28, 30) to the collection protocol stored within processor 60 for the process being monitored at step 106. If the liquid collection device 12 is not correct for the desired collection profile, verification step 76 returns the user to assembly step 74 so that a correct collection device can be used.

If the liquid collection device 12 is correct, verification step 76 logs liquid collection device 12 as being previously used within processor 60 at step 108 and instructs the operator at connection step 78 to place the liquid collection device in liquid communication with the processing line or vessel via HMI 56. As discussed in detail above, liquid collection device 12 is placed in liquid communication with the processing line or vessel by interconnecting two-part connector 38.

As discussed above, containers 28, 30 are described as being bags. However, it is contemplated by the present disclosure for containers 28, 30 to be any desired sterile container. Referring now to FIGS. 9a through 9c, alternate exemplary embodiments of containers 28, 30 are shown and are indicated using multiples of one hundred.

In FIG. 9a, container 228, 230 is illustrated as a fluid holding transport box. Container 228, 230 can be permanently or removably connected to liquid collection device 12. When removably connected, container 228, 230 includes a connector 239 such as, but not limited to Luer lock connector, for connection to liquid collection device 12.

When containers 28, 30 are bags, the containers are typically ventless bags that can expand as fluid is diverted into the bag by workstation 10. However, container 228, 230 is sufficiently rigid such that the container further includes a sterile vent 240. Vent 240 allows gas within container 228, 230 to exit the container as the liquid is diverted into the container. Moreover, vent 240 preferably prevents gas outside of container 228, 230 from entering the container and prevents liquid inside the container from exiting the container. Vent 240 can be any sterile vent such as, but not limited to, the PHARMAVENT vent and the Fine Spike Vent, both of which are commercially available from CliniMed Holdings Limited.

Of course, it should be recognized that it is contemplated by the present disclosure for the collapsible bags to include a sterile vent thereon as needed.

In FIG. 9b, container 328, 330 is illustrated as a fluid holding bottle. Again, container 328, 330 can be permanently or removably connected to liquid collection device 12 and therefore can optionally include a connector 339 for connection to the liquid collection device. Additionally, container 328, 330 is sufficiently rigid such that the container further includes a sterile vent 340 as discussed above.

In FIG. 9c, container 428, 430 is illustrated as a fluid holding syringe. Again, container 428, 430 can be permanently or removably connected to liquid collection device 12 and therefore can optionally include a connector 439 for connection to the liquid collection device.

Container 428, 430 includes a chamber 442 with a piston 444 slideably received therein. Before use, piston 444 is pressed into chamber 442 so that a volume of gas within container 428, 430 is minimized. As workstation 10 diverts liquid into container 428, 430, piston 440 is pushed or slid within chamber 442 such that the fluid holding syringe does not require a separate vent.

As disclosed herein, the liquid collection containers for both product and waste can be any flexible or rigid container, bottle or carpule that allows for the diversion of liquid into the container, while allowing gas within the container to either vent or allowing the container itself to expand or move to accommodate the input liquid.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the present disclosure.

What is claimed is:

1. A method of automatically collecting liquid from a processing line, comprising:
    placing an input conduit of a liquid collection device in liquid communication with the processing line;
    operatively coupling said input conduit to a peristaltic pump and to an input of a valve block having a plurality of three-way valves;
    operatively coupling said valve block to a valve actuator so that each of said plurality of three-way valves is movable by a different portion of said valve actuator among an off position, a flush position, and a collection position;
    controlling said valve actuator to move all of said plurality of three-way valves to said flush position and turning on said peristaltic pump so that liquid from said processing line is pumped through said valve block to a waste container in liquid communication with an output of said valve block; and
    controlling said valve actuator to move a particular valve of said plurality of three-way valves to said collection position and to move any of said plurality of three-way valves upstream of said particular valve to said flush position while said peristaltic pump remains on, said particular valve being associated with a particular collection container so that liquid from said processing line is pumped through said valve block to said particular collection container.

2. The method of claim 1, further comprising controlling said valve actuator to move any of said plurality of three-way valves downstream of said particular valve to said off position.

3. A method of automatically collecting liquid from a processing line, comprising:
    placing an input conduit of a liquid collection device in liquid communication with the processing line;
    operatively coupling said input conduit to an input of a valve block having a plurality of valves;
    operatively coupling said valve block to a valve actuator so that each of said plurality of valves is movable by a different portion of said valve actuator between a first position and a second position;
    controlling said valve actuator to move all of said plurality of valves to said first position so that liquid from said processing line can flow through said valve block to an output of said valve block; and
    controlling said valve actuator to move a particular valve of said plurality of valves to said second position and to move any of said plurality of valves between said input conduit and said particular valve to said first position so that liquid from said processing line flows through said valve block from said input conduit and said particular valve to a collection container.

4. The method of claim 3, further comprising connecting a waste container to said output conduit.

5. The method of claim 4, wherein said waster container has a ratio of volume to product volume of said collection container of 20:1.

6. The method of claim 3, further comprising placing said valve actuator in communication with a processor.

7. The method of claim 6, comprising placing a label printer in communication with said processor.

8. The method of claim 6, further comprising placing a liquid edge detector in communication with said processor.

9. The method of claim 6, comprising placing a sensor in communication with said processor, said sensor being configured to detect an environmental condition.

10. The method of claim 6, further comprising controlling said processor to read information from a machine readable label on said valve block, said information comprising physical characteristics of said collection container.

11. The method of claim 10, wherein said physical characteristics are selected from the group consisting of a lot number, an expiration date, a number of said collection containers, a volume of each of said collection containers, a volume of a waste collection container, and any combinations thereof.

12. The method of claim 6, further comprising communicating a flow rate through said input conduit from a disposable flow meter associated with said input conduit to said processor.

13. The method of claim 6, further comprising operatively coupling said input conduit to a pump in communication with said processor.

14. The method of claim 13, wherein said pump comprises a peristaltic pump.

15. The method of claim 13, further comprising controlling said pump and said valve actuators via an algorithm resident on said processor.

16. The method of claim 15, wherein said algorithm is configured to:
- move all of said plurality of valves to an off position and place said pump in an off state when no collection or flushing is required,
- move all of said plurality of valves to said first position and place said pump in an on state for a predetermined flush time period when flushing is required, and
- move a respective one of said plurality of valves to said second position, move any of said plurality of valves upstream of said respective one to said first position, and place said pump to said on state for a predetermined collection time period when a collection is required.

17. The method of claim 3, wherein the step of placing said input conduit in liquid communication with the processing line comprises connecting a first part of a two-part aseptic connector on said input conduit to a second part of said two-part aseptic connector on the processing line.

18. The method of claim 3, wherein said collection container is a container selected from the group consisting of a bag, a vented bottle, a vented box, a syringe, and any combinations thereof.

* * * * *